United States Patent [19]

Slinkard et al.

[11] 4,200,764
[45] Apr. 29, 1980

[54] OXIDATION OF ALIPHATIC HYDROCARBONS WITH HIGH STRENGTH HYDROCARBON OXIDATION CATALYST

[75] Inventors: William E. Slinkard, Corpus Christi, Tex.; Anthony B. Baylis, Berkeley Heights, N.J.; Michael P. Hughes, Odessa, Tex.

[73] Assignee: Celanese Corporation, New York, N.Y.

[21] Appl. No.: 859,896

[22] Filed: Dec. 12, 1977

[51] Int. Cl.$^2$ .................. C07C 51/20; C07C 53/08
[52] U.S. Cl. ........................... 562/549; 252/467; 260/604 R; 562/536; 562/542; 562/547; 562/548; 585/654
[58] Field of Search ............... 260/533 R; 252/467; 562/549, 548, 542, 536

[56] References Cited

U.S. PATENT DOCUMENTS

| | | | |
|---|---|---|---|
| 3,704,317 | 11/1972 | Yamashita et al. | 260/533 R |
| 3,907,833 | 9/1975 | Slinkard et al. | 260/533 R |

FOREIGN PATENT DOCUMENTS 166670  11/1964  U.S.S.R. ............................ 260/533 R

*Primary Examiner*—Vivian Garner
*Attorney, Agent, or Firm*—Linn I. Grim

[57] ABSTRACT

The present invention provides an unsupported catalyst with superior crush strength for use in a vapor phase reaction for the high yield conversion of lower aliphatic hydrocarbons such as n-butane to corresponding monocarboxylic acids used as acetic acid. The catalyst is prepared by the reduction of a vanadium oxide containing chromium catalyst.

10 Claims, No Drawings

OXIDATION OF ALIPHATIC HYDROCARBONS WITH HIGH STRENGTH HYDROCARBON OXIDATION CATALYST

BACKGROUND OF THE INVENTION

Processes for producing lower aliphatic monocarboxylic acids such as acetic acid by the vapor phase oxidation of lower aliphatic hydrocarbons are known. For example, acetic acid is prepared by the vapor phase oxidation of butane according to the following equation:

$$C_4H_{10} + 5/2 O_2 \rightarrow 2 CH_3COOH + H_2O.$$

However, processes for the oxidation of hydrocarbons in the vapor phase by means of oxygen-containing gases have not proven entirely satisfactory primarily due to the excessive formation of undesirable carbon oxides, and to the difficulty in maintaining control of the highly exothermic oxidation reaction. U.S. Pat. No. 3,395,159 provides an improved process wherein the oxidation of hydrocarbons is performed in a reactor system having fused vanadium oxide catalyst coated on the inner surface of the reactor, which system has the advantage of better temperature control and isothermal operation. The use of early catalysts, such as vanadium pentoxide, either supported or unsupported, for the vapor phase oxidation of lower aliphatic hydrocarbons generally results in yields and process efficiencies which fall substantially short of economic potential. Also, the resulting products are often impure due to a lack of selectivity when such catalysts are employed.

Neat (i.e., unsupported) reduced vanadium oxides such as vanadium tetroxide have been suggested as a remedy for the above disadvantages but heretofore the use of the catalysts in the vapor phase oxidation of lower aliphatic hydrocarbons has resulted in inefficient processes which lack a high degree of selectivity. Furthermore, reduced vanadium oxides in neat form (pellets) lose crush strength during use. This is extremely critical for if the loss of crush strength is excessive such that extensive catalyst fines are developed, the pressure drop over the reactor will become too great to operate the unit thus requiring the catalyst to be removed and recharged. This, of course, is an expensive and time consuming operation that may result in the whole process being too uneconomical to be commercially feasible.

One method utilized in the prior art to eliminate this crush strength loss is to support the reduced vanadium oxide on an inert and rigid support.

Typical of the elaborate steps taken to obviate the crush strength loss via a support is the procedure disclosed in U.S. Pat. No. 3,962,137 wherein an abrasion resistant catalyst is produced for the oxidation of lower aliphatic hydrocarbons by intimately mixing an aqueous suspension of colloidal non-porous silica particles with a water soluble metal salt which is decomposable by heat to a metal oxide, calcining the mixture, adding a further amount of the aqueous suspension of colloidal non-porous silica particles, and drying this catalyst composition. The essence of this patented invention is the formation of an outer porous net of non-porous colloidal silica particles over the calcined mixture of metal oxide and non-porous colloidal silica.

OBJECTS AND SUMMARY OF THE INVENTION

Accordingly, a general object of the present invention is to avoid or substantially alleviate the above problems of the prior art in a simple and straightforward manner.

A more specific object is the provision of the process for the production of acetic acid by the vapor phase oxidation of lower aliphatic hydrocarbons.

Another and primary object of the invention is to provide a highly efficient process for the production of acetic acid by the vapor phase oxidation of lower aliphatic hydrocarbons using an unsupported catalyst with significantly improved physical strength thereby obviating the attendant processing steps necessary to produce the supported catalyst.

These and other objects are achieved by a process for preparing acetic acid by the vapor phase oxidation of a lower aliphatic hydrocarbon such as n-butane, which process comprises reacting a lower aliphatic hydrocarbon and an oxygen-containing gas in the vapor phase, preferably in the presence of steam, and a catalytic amount of a reduced vanadium and chromium oxide compound. The essence of the invention lies in the discovery that the addition of from about 1 to about 50 mole percent of chromium oxide calculated as chromium (III) oxide to a reduced vanadium oxide yields an extremely crush-resistant catalyst which when utilized in a vapor phase oxidation of a lower aliphatic hydrocarbon such as butane, realizes comparable efficiency to acetic acid when compared to use of a catalytic amount of reduced vanadium oxide alone.

Other objects and advantages of the present invention will become apparent from the following description of the preferred embodiments.

THE PREFERRED EMBODIMENTS

The pre-reduced catalyst composition of the instant invention can be prepared by at least three different techniques. A preferred method is to physically mix vanadium pentoxide and chromium sesquioxide and heat the mixture at temperatures above about 650° C. until a homogeneous melt is achieved.

Another method to prepare these catalyst precursors is to prepare an aqueous solution of ammonium metavanadate or decavanadate and chromium (III) nitrate; filter and dry.

The most preferred way for producing the vanadium/chromium oxide precursor is to prepare an aqueous mixture, i.e., slurry or solution, of vanadyl oxalate and chromium acetate and dry same.

The catalyst should contain from about 1 to about 50 mole percent of chromium oxide calculated as chromium (III) oxide preferably from about 2 to about 30; and most preferably from about 3 to about 20 mole percent.

The reduction of the oxide precursors to an activated form can take place by art-recognized techniques in any conventional reducing medium such as butane, butane-air, hydrogen, carbon monoxide and ammonia and the activation of the metal salts can be realized by calcining at high temperatures in an inert atmosphere.

These reductions should take place at temperatures high enough to affect reasonable reduction rates yet below about 600° C. to avoid melting of the oxides. This process is continued until all of the vanadium oxide is in reduced state as can be determined by oxidation product measurements in the vent gas, e.g. cessation of H₂O formation during hydrogen reduction or CO₂ formation during CO reduction. Of course, if the reduction is accomplished under elevated pressures such as for example from about 150 to about 250 psig, the reduction time is significantly reduced.

In the process of the present invention, a lower aliphatic hydrocarbon is reacted with an oxygen-containing gas in the presence of a catalytically effective amount of the above-described reduced vanadium/chromium oxide catalyst to produce acetic acid.

By "lower aliphatic hydrocarbons" is meant any saturated or unsaturated aliphatic hydrocarbon containing from 2 to 10 carbon atoms. These lower aliphatic hydrocarbons include alkanes, alkenes, and alkynes such as ethylene, propylene, butene, propane, butane, pentane, octane and their isomers. Particularly preferred aliphatic hydrocarbons are the alkanes and alkenes including propane, butane, butene, isobutane, isobutene and mixtures thereof.

The production of acetic acid from butane can give particularly advantageous results.

By the term "reduced vanadium oxide" or "reduced vanadium pentoxide" is meant a vanadium oxide in which the vanadium ions have a valence less than five. A lower oxidation state of vanadium ions is an essential feature of the present invention catalysts. This is based on the observation that vanadium pentoxide (i.e., a catalyst containing vanadium ions with a valence of 5) is not an active catalyst, and it is, therefore, advantageous to exclude vanadium pentoxide from the catalyst compositions to the greatest extent possible. The reduced vanadium oxides employed in the catalyst of the present invention are all intermediate in oxidation states, i.e., between $V_2O_5$ and/or a $V_6O_{13}$. The average valence of the vanadium ions in these oxides ranges from 3 to about 4.5.

The oxygen necessary as a reactant in the present process may be practically any molecular oxygen-containing gas such as molecular oxygen or air. Also the molecular oxygen-containing gas may be one wherein molecular oxygen is mixed in varying amounts with an inert diluent gas such as nitrogen, argon or a carbon oxide. The lower aliphatic hydrocarbon and oxygen-containing gas can be reacted within a wide range of molar ratios. However, it is an essential feature of the invention process that the quantity of oxygen gas in the feed stream be the least required to convert efficiently the hydrocarbon stream to acetic acid consistent with necessary temperature control and retention of catalyst activity. It is important that the vanadium oxide catalyst is not oxidized to vanadium pentoxide. Even the presence of a small amount of vanadium pentoxide is effective in reducing the yield of acetic acid. The quantity of oxygen gas in the feed stream usually is maintained in the range between about 0.05 and 1 mole per mole of lower aliphatic hydrocarbon, preferably in the range of from about 0.05 to about 0.30.

In a preferred embodiment of the invention process, water is included in the feed stream in a quantity between about 0.1 and 2.0 moles per mole of lower aliphatic hydrocarbon. The presence of water vapor in the oxidation reaction system can increase the yield of acetic acid by as much as 10% in the case where the hydrocarbon feed stream is normal butane.

The present process is carried out at a temperature generally between about 180° and 400° C., typically between about 200° and 350° C., and preferably between about 220° and 300° C. The present process can be carried out at subatmospheric, atmospheric, or superatmospheric pressures, but generally from about 0.1 to about 50 atmospheres, typically from about 0.5 to about 30 atmospheres, and preferably from about 1 to about 20 atmospheres. The contact time of the reactants with the catalyst is generally between about 0.1 and 100 seconds, and typically between about 0.25 and 50 seconds. The contact time as used herein is meant the contact time adjusted to 25° C. and 1 atmospheric pressure (i.e., standard temperature and pressure, denoted by STP). Thus, the contact time is calculated by dividing the volume of the catalyst bed (including voids) by the volume per unit time flow rate of the reactants at STP.

The process of the present invention may be carried out continuously and the catalyst may be present in various forms such as in one or more fixed beds or as a fluidized system.

Portions of the reactants which do not undergo reaction may be recycled if necessary. Selected intermediate products, such as butenes and acetaldehydes, are preferably recycled also. The desired acetic acid product may be separated from any impurities by condensation followed by fractionation and aqueous or nonaqueous extraction of the product from the unreacted lower aliphatic hydrocarbon. In this specification, the terms conversion and efficiency are defined as follows:

$$\text{conversion, \%} = \frac{\text{moles lower aliphatic hydrocarbon or oxygen converted}}{\text{moles lower aliphatic hydrocarbon or oxygen fed}} \times 100$$

$$\text{carbon efficiency to component } i\ (\%) = \frac{\text{moles component } i \text{ formed} \times \text{carbon atoms per mole of component } i}{\text{total moles of carbon in all products analyzed}} \times 100$$

Acetic acid is produced by the present process with a conversion (based on oxygen) generally of at least 90%, often at least about 95%; a conversion based on lower aliphatic hydrocarbon (which, as noted above, is present in substantial excess) generally of at least about 1%, typically at least about 3%, often at least about 5%; and a carbon efficiency of generally at least about 50%, typically at least about 55%, often at least about 60% with recycled intermediates.

As indicated hereinabove, the present process is useful for preparing acetic acid with improved yield and process efficiency of the catalyst with an unsupported catalyst of superior crush strength. The recovery of the product stream and the separation of the acetic acid from the acetaldehyde, maleic acid and other by-products can be accomplished by conventional procedures. U.S. Pat. No. 3,624,148 describes a method for the separation of acetic acid from maleic acid.

The present invention is further illustrated by the following examples. All parts and percentages in the examples as well as in the specification and claims are by weight unless otherwise specified. The reactants and other specific ingredients are presented as being typical, and various modifications can be devised in view of the foregoing disclosure within the scope of the invention.

EXAMPLES I–VIII

Catalyst Preparation

The following procedures are used to prepare vanadium/chromium oxide catalysts as indicated using the appropriate quantities of reagents.

Vanadium pentoxide and chromium sesquioxide (where appropriate) are physically mixed, placed in a quartz dish, heated to about 825° C. and held at that temperature from about one to two hours. The catalyst precursor is then removed from the furnace and allowed to cool to room temperature. The resulting crystalline solid is crushed and screened to 20/30 mesh. All the powders below are pretreated with a butane/air mixture (1:1 molar ratio) at 370° C. for 16 hours at atmospheric pressure.

| Catalyst Identification | Vanadium Source | Chromium Source |
|---|---|---|
| Catalyst A | $V_2O_5$ 60.0 grams | $Cr_2O_3$ 0.00 grams |
| B | $V_2O_5$ 49.1 grams | $Cr_2O_3$ 0.91 grams |
| C | $V_2O_5$ 51.8 grams | $Cr_2O_3$ 2.28 grams |
| D | $V_2O_5$ 49.1 grams | $Cr_2O_3$ 5.52 grams |
| E | $V_2O_5$ 72.7 grams | $Cr_2O_3$ 15.2 grams |
| F | $V_2O_5$ 36.6 grams | $Cr_2O_3$ 30.4 grams |

| G | Ammonium metavanadate (4.68 grams) is dissolved in 140 milliliters of hot water and combined with 144.0 grams of $Cr(NO_3)_3 \cdot 9H_2O$ dissolved in 100 milliliters of water. The water is removed on a rotary evaporator and the resulting solid calcined at 550° C. for six hours. The recovered solid is pressed into pellets and then crushed and screened to 20/30 mesh. |
|---|---|
| H | Commercially available reagent grade chromium sesquioxide is pressed into pellets and then crushed and screened to 20/30 mesh. |

EXAMPLES IX–XVI

The following examples illustrate the use of the above prepared catalysts in the vapor phase oxidation of butane to acetic acid.

A U-shaped titanium or stainless steel tube is employed to hold the catalyst charge. The tube is about 70–80 centimeters tall with an inside diameter of about 1 centimeter. The usual catalyst charge is about 10 grams of 20/30 mesh material. The reactor is heated to the desired temperature using a fluidized sand bath. Flow rates of the lower aliphatic hydrocarbons and air (or oxygen) are determined at normal temperatures and pressures (STP) with a soap-film bubble meter. Steam is introduced as water at a known flow rate and flashed to steam with the flow rate of steam calculated by application of the ideal gas law. After the reactor with the catalyst charge is installed in the system, the lower aliphatic hydrocarbons and air (or oxygen) and steam mixture is immediately diverted through the catalyst to minimize any air oxidation of the catalyst (fairly rapid at elevated temperatures) if the catalyst had been activated (reduced) external to the reactor. After the flow rates are stabilized, the temperature of the sand bath (initially about 200°–210° C.) is then raised until nearly all of the oxygen is consumed in the reaction. Material balances are then obtained at this temperature. Reactions can be conducted at or near atmospheric pressure but it is preferred to operate the reactor under pressure so that cooling water can be used to condense the butane recycle stream. When the reactions are at atmospheric pressure, the reaction products plus unreacted lower aliphatic hydrocarbons and steam are passed through a condensor after leaving the heated reaction zone, to remove the liquid products and water from the vent stream. The vent stream, now containing primarily lower aliphatic hydrocarbons, carbon oxides and nitrogen is analyzed continuously on a Fisher-Hamilton gas partitioner. The liquid sample is collected after the end of the run and analyzed by standard gas chromatograph techniques. Total acid content (primarily acetic acid) is determined by titration with base.

The following represents typical results realized when the catalysts of Examples I–VIII are utilized in the above-described process.

|  | A | B | C | D | E | F | G | H |
|---|---|---|---|---|---|---|---|---|---|---|---|---|---|---|---|
| Steam | Yes | No | Yes | No | Yes | No | Yes | No | Yes | No | Yes | No | Yes | No | Yes |
| Reactor Temperature (°C.) | 244 | 235 | 230 | 241 | 236 | 235 | 230 | 258 | 242 | 226 | 225 | 260 | 256 | 335 | 346 |
| Composition (mole %) $Cr_2O_3$ | 0 | | 2 | | 5 | | 12 | | 20 | | 50 | | 90 | | 100 |
| Carbon Efficiency (%) | | | | | | | | | | | | | | | |
| Acetic Acid | 63 | 48 | 57 | 59 | 64 | 54 | 66 | 52 | 59 | 49 | 53 | 37 | 43 | 0 | 0 |
| Maleic Acid | (not analyzed) | 3 | 3 | 2 | 0 | 4 | 0 | 3 | 2 | 3 | 0 | 3 | 0 | 0 | 0 |
| $CO/CO_2$ | 36 | 48 | 40 | 39 | 36 | 42 | 34 | 44 | 39 | 48 | 47 | 60 | 57 | 100 | 100 |

(1) Atmospheric Pressure
(2) Butane:Air:$H_2O$ Ratio = 1:1:0 or 1:1:0.13
(3) Oxygen conversion in each example >99%

EXAMPLE XVII

The following example illustrates the preparation and use of a preferred catalyst of the instant invention.

To a slurry of 364 grams of $V_2O_5$ in 350 milliliters of water is added slowly with stirring 757 grams of oxalic acid ($H_2C_2O_4 \cdot 2H_2O$) dissolved in 1500 milliliters of water. The reaction mixture is stirred for about two hours at 80° C. then stirred for about 16 hours at ambient temperature and filtered. This procedure is repeated and the filtrates combined. To the combined filtrate is added 45.8 grams of chromium hydroxide dissolved in a small amount of acetic acid (0.44 moles of chromium). The solution is spray-dried at 165°–170° C. The dry powder is placed in a quartz tube and heated to 200° C. under a nitrogen atmosphere. The temperature is raised to 400° C. over a five hour period; held at 400° C. for about 16 hours; and then cooled to ambient temperature still under a nitrogen atmosphere. The recovered catalyst powder is mixed with 2% graphite and pressed into cylindrical pellets (⅛ inch diameter×3/16 inch length).

The following represents typical process parameters and results realized when the catalyst of this example is utilized in the process aforedescribed in Examples IX-–XVI in an appropriately sized fixed bed tubular reactor, i.e., a tube of about 0.824 inch inside diameter and about five feet long.

| Reactor Pressure (psig) | 140 |
|---|---|

| -continued | |
|---|---|
| Reactor Temperature (°C.) | 272 |
| Reactant Feed Rate (1/min) (STP) | |
| Butane | 14.8 |
| Oxygen | 1.6 |
| Steam | 13.1 |
| Conversion (%) | |
| Butane | 3.3 |
| Oxygen | 98 |
| Carbon Efficiency to Products (%) | |
| Butenes | 18 |
| Acetic Acid | 45 |
| Acetaldehyde | 3.4 |
| Carbon Oxides | 30 |

| Catalyst crush strength after use (about 40 hours)* | |
|---|---|
| Top of catalyst bed | 22 psi |
| Middle of catalyst bed | 20 psi |
| Middle of catalyst bed | 18 psi |
| Bottom of catalyst bed | 13 psi |
| Catalyst crush strength unused, about | 22 psi |

*Crush strength was determined by crushing at least 30 pellets (lying on their sides, that is with the axis of the pellet transverse to the crushing force) on Dillon Force Gauges (0 to 25 lbs. and 0 to 50 lbs.) in a Paar pellet press.

EXAMPLE XVIII

This example illustrates the very low crush strengths realized with unsupported reduced vanadium oxide catalyst when chromium oxide is not incorporated.

About 650–750 g of vanadyl oxalate prepared by the reaction of vanadium pentoxide with oxalic acid using a standard technique is placed in the center of a two inch quartz tube. The quartz tube and contents are purged of air with nitrogen and under a steady stream of nitrogen heated to 200° C. The temperature is increased from 200° to 425° C. over a period of 5 hours, held at that temperature for about 16–24 hours, and then cooled rapidly to room temperature still under a steady flow of nitrogen. About 290–330 g of reduced vanadium oxide is recovered. The reduced vanadium oxide is mixed with 2 weight percent graphite and pressed into pellets (3/16" diameter × 3/32" length) on a rotary pellet press. These pellets are then charged to a reactor without further treatment and a butane oxidation is accomplished as described in Examples IX–XVI. The following represents typical process parameters and results:

| | |
|---|---|
| Reactor Pressure (psig) | 180 |
| Reactor Temperature (°C.) | 270 |
| Reactant Feed Rate (1/min) (STP) | |
| Butane | 12.2 |
| Oxygen | 3.2 |
| Steam | 11.4 |
| Conversion (%) | |
| Butane | 4.2 |
| Oxygen | 99 |
| Carbon Efficiency to Products (%) | |
| Butenes | 15 |
| Acetic Acid | 46 |
| Acetaldehyde | 3.3 |
| Carbon Oxides | 29 |

| Catalyst crush strength after use (about 110 hours) | |
|---|---|
| Top of catalyst bed | 9.9 psi |
| Middle of catalyst bed | 8.6 psi |
| Middle of catalyst bed | 4.2 psi |
| Middle of catalyst bed | 3.5 psi |
| Bottom of catalyst bed | 1.7 psi |
| Catalyst crush strength unused, about | 14.1 psi |

While all of the above runs are conducted with a fixed bed reactor, it is quite obvious that the superior crush strength of the instant catalyst makes it ideally suited for fluid bed operations.

We claim:

1. A process for preparing acetic acid by the vapor phase oxidation of alkanes containing from 2 to 10 carbon atoms with an oxygen containing gas in the vapor phase in the presence of steam and a catalytic amount of a catalyst consisting essentially of a reduced vanadium oxide catalyst containing from about 1 to about 50 mols percent chromium oxide calculated as chromium (III) oxide.

2. The process of claim 1 wherein the reduced vanadium oxide catalyst contains from about 2 to about 30 mole percent chromium oxide calculated as chromium (III) oxide.

3. The process of claim 1 wherein the reduced vanadium oxide catalyst contains from about 3 to about 20 mole percent chromium oxide calculated as chromium (III) oxide.

4. The process of claim 1 wherein the molar ratio of oxygen to alkane is from about 0.05 to about 0.30.

5. The process of claim 1 wherein the molar ratio of steam to alkane is from about 0.1 to 2.0.

6. The process of claim 1 wherein the temperature of the process is from about 220° C. to about 300° C.

7. The process of claim 1 wherein the pressure of the process is from about 1 to about 20 atmospheres.

8. The process of claim 1 wherein the alkane is n-butane.

9. The process of claim 1 wherein the alkane feed stream contains recycled butenes.

10. The process of claim 1 wherein the alkane feed stream contains recycled butenes and acetaldehyde.

* * * * *